(12) United States Patent
Mallikarjunagoud (10) Patent No.: US 12,070,554 B2
(45) Date of Patent: Aug. 27, 2024

(54) PNEUMATIC CONNECTOR APPARATUS AND METHOD

(71) Applicant: HILL-ROM SERVICES PTE. LTD., Singapore (SG)

(72) Inventor: Mallikarjunagoud, Singapore (SG)

(73) Assignee: HILL-ROM SERVICES PTE. LTD., Singapore (SG)

(*) Notice: Subject to any disclaimer, the term of this patent is extended or adjusted under 35 U.S.C. 154(b) by 665 days.

(21) Appl. No.: 17/082,200

(22) Filed: Oct. 28, 2020

(65) Prior Publication Data

US 2021/0138175 A1    May 13, 2021

Related U.S. Application Data

(60) Provisional application No. 62/933,569, filed on Nov. 11, 2019.

(51) Int. Cl.
*A61M 16/08* (2006.01)
*A61M 16/00* (2006.01)

(52) U.S. Cl.
CPC ...... *A61M 16/0816* (2013.01); *A61M 16/022* (2017.08); *A61M 2202/0208* (2013.01); *A61M 2205/02* (2013.01)

(58) Field of Classification Search
CPC ......... F16L 37/113; F16L 37/56; F16L 37/60; F16D 1/00; A61M 16/0096; A61M 39/10; A61M 39/1011; A61M 39/105; A61M 2039/1077; A61M 16/0816; A61M 25/0026; A61M 2039/1016; A61M 2039/1027; A61M 16/022; A61M 2202/0208; A61M 2205/02; A61M 16/0875; A61M 2205/025

See application file for complete search history.

(56) References Cited

U.S. PATENT DOCUMENTS

| 402,779 A | 5/1889 | Steiniioff |
| 1,150,238 A | 8/1915 | Winbray |
| 2,475,468 A | 7/1949 | Andrews |
| 2,510,125 A | 6/1950 | Meakin |
| 2,788,991 A | 4/1957 | Neuhauser |

(Continued)

FOREIGN PATENT DOCUMENTS

| DE | 4232298 A1 | 3/1994 |
| EP | 1159918 A1 | 12/2001 |

(Continued)

OTHER PUBLICATIONS

Extended European Search Report for EP 20205983 dated Mar. 31, 2021, 7 pages.

(Continued)

*Primary Examiner* — Samchuan C Yao
*Assistant Examiner* — Tina Zhang
(74) *Attorney, Agent, or Firm* — Barnes & Thornburg LLP (57) ABSTRACT

A respiratory therapy device includes a respiratory control unit, a respiratory circuit, and a multi-port connector. The respiratory control unit is configured to provide at least one respiratory therapy for a user. The respiratory circuit is coupled to the respiratory control unit to deliver the respiratory therapy to the user. The multi-port connector interconnects the respiratory circuit to the respiratory control unit.

17 Claims, 5 Drawing Sheets

(56) References Cited

U.S. PATENT DOCUMENTS

| | | | |
|---|---|---|---|
| 2,837,749 A | 6/1958 | Gross | |
| 3,083,707 A | 4/1963 | Seeler | |
| 3,291,122 A | 12/1966 | Engstrom et al. | |
| 3,301,255 A | 1/1967 | Thompson | |
| 3,469,863 A | 9/1969 | Riester et al. | |
| 3,537,448 A | 11/1970 | Liston | |
| 3,561,444 A | 2/1971 | Eoucher | |
| 3,584,621 A | 6/1971 | Bird et al. | |
| 3,861,386 A | 1/1975 | Harris et al. | |
| 4,054,134 A | 10/1977 | Kritzer | |
| 4,062,358 A | 12/1977 | Kritzer | |
| 4,182,599 A | 1/1980 | Brown et al. | |
| 4,245,633 A | 1/1981 | Erceg | |
| 4,436,090 A | 3/1984 | Darling | |
| 4,558,710 A | 12/1985 | Eichler | |
| 4,601,465 A | 7/1986 | Roy | |
| 4,630,847 A | 12/1986 | Blenkush | |
| 4,635,857 A | 1/1987 | Hughes | |
| 4,703,957 A | 11/1987 | Blenkush | |
| 4,770,164 A | 9/1988 | Lach et al. | |
| 4,951,659 A | 8/1990 | Weiler et al. | |
| 4,964,404 A | 10/1990 | Stone | |
| 4,973,047 A | 11/1990 | Norell | |
| 4,981,295 A | 1/1991 | Belman et al. | |
| 5,018,517 A | 5/1991 | Liardet | |
| 5,027,809 A | 7/1991 | Robinson | |
| 5,067,707 A | 11/1991 | Kohnke | |
| 5,069,449 A | 12/1991 | Wardwell | |
| 5,107,830 A | 4/1992 | Younes | |
| 5,127,400 A | 7/1992 | Devries et al. | |
| 5,150,291 A | 9/1992 | Cummings et al. | |
| 5,193,529 A | 3/1993 | Labaere | |
| 5,261,394 A | 11/1993 | Mulligan et al. | |
| 5,277,175 A | 1/1994 | Riggs et al. | |
| 5,322,057 A | 6/1994 | Raabe et al. | |
| 5,355,873 A | 10/1994 | Del Bon et al. | |
| 5,390,665 A | 2/1995 | Leach | |
| 5,398,676 A | 3/1995 | Press et al. | |
| 5,413,110 A | 5/1995 | Cummings et al. | |
| 5,423,313 A | 6/1995 | Olsson et al. | |
| 5,439,430 A | 8/1995 | Rubens et al. | |
| 5,451,190 A | 9/1995 | Liardet | |
| 5,535,738 A | 7/1996 | Estes et al. | |
| 5,542,416 A | 8/1996 | Chalvignac | |
| 5,547,440 A | 8/1996 | Rubens et al. | |
| 5,570,682 A | 11/1996 | Johnson | |
| 5,598,839 A | 2/1997 | Niles et al. | |
| 5,613,945 A | 3/1997 | Cai et al. | |
| 5,617,847 A | 4/1997 | Howe | |
| 5,664,562 A | 9/1997 | Bourdon | |
| 5,666,945 A | 9/1997 | Davenport | |
| 5,713,349 A | 2/1998 | Keaney | |
| 5,823,179 A | 10/1998 | Grychowski et al. | |
| 5,829,429 A | 11/1998 | Hughes | |
| 5,906,198 A | 5/1999 | Flickinger | |
| 5,937,857 A | 8/1999 | Caterini et al. | |
| 5,938,117 A | 8/1999 | Ivri | |
| 5,950,619 A | 9/1999 | Van Der Linden et al. | |
| 5,964,223 A | 10/1999 | Baran | |
| 5,970,974 A | 10/1999 | Van Der Linden et al. | |
| 5,992,894 A * | 11/1999 | Eybergen | F16L 39/00 |
| | | | 29/469 |
| 6,044,841 A | 4/2000 | Verdun et al. | |
| 6,058,932 A | 5/2000 | Hughes | |
| 6,076,520 A | 6/2000 | Cooper | |
| 6,079,413 A | 6/2000 | Baran | |
| 6,085,740 A | 7/2000 | Ivri et al. | |
| 6,085,746 A | 7/2000 | Fox | |
| 6,116,233 A | 9/2000 | Denyer et al. | |
| 6,152,134 A | 11/2000 | Webber et al. | |
| 6,170,882 B1 | 1/2001 | Prest | |
| 6,210,345 B1 | 4/2001 | Van Brunt | |
| 6,234,167 B1 | 5/2001 | Cox et al. | |
| 6,240,919 B1 | 6/2001 | MacDonald et al. | |
| 6,355,002 B1 | 3/2002 | Faram et al. | |
| 6,363,932 B1 | 4/2002 | Forchione et al. | |
| 6,402,046 B1 | 6/2002 | Loser | |
| 6,405,934 B1 | 6/2002 | Hess et al. | |
| 6,412,481 B1 | 7/2002 | Bienvenu et al. | |
| 6,415,791 B1 | 7/2002 | Van Brunt | |
| 6,425,393 B1 | 7/2002 | Lurie et al. | |
| 6,427,690 B1 | 8/2002 | McCombs et al. | |
| 6,450,163 B1 | 9/2002 | Blacker et al. | |
| 6,467,476 B1 | 10/2002 | Ivri et al. | |
| 6,526,976 B1 | 3/2003 | Baran | |
| 6,540,153 B1 | 4/2003 | Ivri | |
| 6,540,154 B1 | 4/2003 | Ivri et al. | |
| 6,546,927 B2 | 4/2003 | Litherland et al. | |
| 6,550,472 B2 | 4/2003 | Litherland et al. | |
| 6,550,476 B1 | 4/2003 | Ryder | |
| 6,557,549 B2 | 5/2003 | Schmidt et al. | |
| 6,568,387 B2 | 5/2003 | Davenport et al. | |
| 6,571,790 B1 | 6/2003 | Weinstein | |
| 6,581,596 B1 | 6/2003 | Truitt et al. | |
| 6,581,598 B1 | 6/2003 | Foran et al. | |
| 6,581,600 B2 | 6/2003 | Bird | |
| 6,588,421 B1 | 7/2003 | Diehl et al. | |
| 6,588,422 B1 | 7/2003 | Berthon-Jones et al. | |
| 6,595,203 B1 | 7/2003 | Bird | |
| 6,598,602 B1 | 7/2003 | Sjoholm | |
| 6,598,603 B1 | 7/2003 | Andersson et al. | |
| 6,609,517 B1 | 8/2003 | Estes et al. | |
| 6,612,303 B1 | 9/2003 | Grychowski et al. | |
| 6,615,831 B1 | 9/2003 | Tuitt et al. | |
| 6,626,175 B2 | 9/2003 | Jafari et al. | |
| 6,631,721 B1 | 10/2003 | Salter et al. | |
| 6,640,806 B2 | 11/2003 | Yurko | |
| 6,644,304 B2 | 11/2003 | Grychowski et al. | |
| 6,644,310 B1 | 11/2003 | Delache et al. | |
| 6,644,311 B1 | 11/2003 | Truitt et al. | |
| 6,663,574 B2 | 12/2003 | Faram et al. | |
| 6,679,258 B1 | 1/2004 | Strom | |
| 6,694,969 B1 | 2/2004 | Heinonen et al. | |
| 6,702,998 B2 | 3/2004 | Conner | |
| 6,708,688 B1 | 3/2004 | Rubin et al. | |
| 6,718,969 B1 | 4/2004 | Rubin et al. | |
| 6,722,362 B2 | 4/2004 | Hete et al. | |
| 6,729,334 B1 | 5/2004 | Baran | |
| 6,737,042 B2 | 5/2004 | Rabinowitz et al. | |
| 6,752,151 B2 | 6/2004 | Hill | |
| 6,776,159 B2 | 8/2004 | Pelerossi et al. | |
| 6,799,605 B1 | 10/2004 | Van Scyoc et al. | |
| 6,805,120 B1 | 10/2004 | Jeffrey et al. | |
| 6,823,866 B2 | 11/2004 | Jafari et al. | |
| 6,848,443 B2 | 2/2005 | Schmidt et al. | |
| 6,851,425 B2 | 2/2005 | Jaffre et al. | |
| 6,854,462 B2 | 2/2005 | Berthon-Jones et al. | |
| 6,904,906 B2 | 6/2005 | Salter et al. | |
| 6,907,881 B2 | 6/2005 | Suki et al. | |
| 6,910,479 B1 | 6/2005 | Van Brunt | |
| 6,915,803 B2 | 7/2005 | Berthon-Jones et al. | |
| 6,932,084 B2 | 8/2005 | Estes et al. | |
| 6,948,497 B2 | 9/2005 | Zdrojkowski et al. | |
| 6,968,840 B2 | 11/2005 | Smith et al. | |
| 7,011,091 B2 | 3/2006 | Hill et al. | |
| 7,036,500 B2 | 5/2006 | Niles et al. | |
| 7,059,324 B2 | 6/2006 | Pelerossi et al. | |
| 7,066,176 B2 | 6/2006 | Jaffe et al. | |
| 7,070,761 B2 | 7/2006 | Rabinowitz et al. | |
| 7,100,607 B2 | 9/2006 | Zdrojkowski et al. | |
| 7,128,069 B2 | 10/2006 | Farrugia et al. | |
| 7,165,547 B2 | 1/2007 | Truitt et al. | |
| 7,188,621 B2 | 3/2007 | DeVries et al. | |
| 7,191,776 B2 | 3/2007 | Niles et al. | |
| 7,191,780 B2 | 3/2007 | Faram | |
| 7,204,245 B2 | 4/2007 | Johnson et al. | |
| 7,210,480 B2 | 5/2007 | Lurie et al. | |
| 7,232,417 B2 | 6/2007 | Plante | |
| 7,302,949 B2 | 12/2007 | Pelerossi et al. | |
| 7,445,607 B2 | 11/2008 | Plante | |
| 7,469,700 B2 | 12/2008 | Baran | |
| 7,472,702 B2 | 1/2009 | Beck et al. | |
| 7,472,705 B2 | 1/2009 | Baran | |
| 7,500,481 B2 | 3/2009 | Delache et al. | |

(56) References Cited

U.S. PATENT DOCUMENTS

| | | | |
|---|---|---|---|
| 7,562,657 B2 | 7/2009 | Blanch et al. | |
| 7,600,511 B2 | 10/2009 | Power et al. | |
| 7,699,054 B2 | 4/2010 | Pelerossi et al. | |
| 9,151,425 B2 | 10/2015 | Faram | |
| 9,272,115 B2 | 3/2016 | Bobey et al. | |
| 9,675,775 B2 | 6/2017 | Bobey et al. | |
| 2001/0004893 A1 | 6/2001 | Biondi et al. | |
| 2002/0020412 A1 | 2/2002 | Gilbert et al. | |
| 2002/0049122 A1* | 4/2002 | Mercado | A63B 21/00181 482/57 |
| 2002/0163194 A1 | 11/2002 | Mintz et al. | |
| 2003/0051731 A1 | 3/2003 | Be'eri et al. | |
| 2003/0136800 A1* | 7/2003 | Brand | A61M 15/009 222/402.13 |
| 2003/0140925 A1 | 7/2003 | Sapienza et al. | |
| 2003/0205229 A1 | 11/2003 | Crockford et al. | |
| 2005/0061318 A1 | 3/2005 | Faram | |
| 2005/0082828 A1* | 4/2005 | Wicks | F16L 37/38 285/320 |
| 2005/0109340 A1 | 5/2005 | Tehrani | |
| 2005/0137614 A1* | 6/2005 | Porter | A61M 1/3655 606/153 |
| 2005/0165334 A1 | 7/2005 | Lurie | |
| 2005/0212286 A1 | 9/2005 | Smith | |
| 2005/0217666 A1 | 10/2005 | Fink et al. | |
| 2006/0084877 A1 | 4/2006 | Ujhazy et al. | |
| 2006/0144398 A1 | 7/2006 | Doshi et al. | |
| 2006/0178245 A1 | 8/2006 | Schiller et al. | |
| 2006/0201500 A1 | 9/2006 | Von Hollen et al. | |
| 2006/0243274 A1 | 11/2006 | Lieberman et al. | |
| 2006/0243282 A1* | 11/2006 | Sackman | A61M 16/08 128/205.22 |
| 2006/0272642 A1 | 12/2006 | Chalvignac | |
| 2007/0017522 A1 | 1/2007 | Be-Eri et al. | |
| 2007/0017523 A1 | 1/2007 | Be-Eri et al. | |
| 2007/0089740 A1 | 4/2007 | Baumert et al. | |
| 2007/0186928 A1 | 8/2007 | Be'Eri | |
| 2008/0000475 A1 | 1/2008 | Hill | |
| 2008/0000477 A1 | 1/2008 | Huster et al. | |
| 2008/0015456 A1 | 1/2008 | McCawley et al. | |
| 2008/0091117 A1 | 4/2008 | Choncholas et al. | |
| 2008/0190429 A1 | 8/2008 | Tatarek | |
| 2008/0283060 A1 | 11/2008 | Bassin | |
| 2009/0020121 A1 | 1/2009 | Bassin | |
| 2009/0232585 A1 | 9/2009 | Gilbreath et al. | |
| 2010/0089561 A1* | 4/2010 | Sharma | F28F 9/0253 165/178 |
| 2010/0263677 A1* | 10/2010 | Thornton | A61F 5/566 128/848 |
| 2011/0100364 A1* | 5/2011 | Faram | F16L 37/113 285/120.1 |
| 2011/0204621 A1 | 8/2011 | Whitaker et al. | |
| 2014/0144446 A1 | 5/2014 | Bobey et al. | |
| 2018/0050183 A1* | 2/2018 | Taylor | A61J 1/2037 |
| 2018/0079334 A1* | 3/2018 | Zheng | B60N 2/366 |

FOREIGN PATENT DOCUMENTS

| | | |
|---|---|---|
| EP | 2317200 A1 | 5/2011 |
| WO | 2007101516 A1 | 9/2007 |
| WO | 2007101525 A1 | 9/2007 |
| WO | 2015197605 A1 | 12/2015 |

OTHER PUBLICATIONS

Japanese Office Action for JP 2020-182356 dated Dec. 21, 2021 with translation.
Airway Clearance Seminar Presentation, Rodney Clarke, 2019.
Decision of Rejection dated Jul. 12, 2022, issued for Japanese Patent Application No. 2020-182356 and its English translation (5 pages).
European Search Report for EP 20205983.8 dated Jan. 31, 2023.
European Examination Report for EP20205983 dated Apr. 30, 2024.

* cited by examiner

PNEUMATIC CONNECTOR APPARATUS AND METHOD

PRIORITY CLAIM

This application claims priority under 35 U.S.C. § 119(e) to U.S. Provisional Application Ser. No. 62/933,569, filed Nov. 11, 2019, which is expressly incorporated by reference herein.

BACKGROUND

The present disclosure relates to a multiple conduit connector that may be used for simultaneously interconnecting multiple tubes. More particularly, the present disclosure relates to a multiple conduit connector including a quick action lock/release mechanism having a self-alignment feature enhancing proper interconnection for each of the individual tubes.

Many applications involve numerous tubes or hoses for conveying gases, liquids, and the like. For example, in robotics numerous tubes or hoses are sometimes needed to provide the desired control and operation of the multiplicity of movements involved. In many hospitals and medical offices in which numerous tools are used, there is a need for a multiplicity of tubes carrying the various control and operating gases or liquids to each of the individual tools or patient interfaces. Regardless of the application, it is oftentimes very desirable to be able to simultaneously disconnect or connect a multiplicity of the individual tubes.

As a result of this need, multiple tube connectors have been developed. Multiple tube connectors typically employ at least two coupling parts having paths for the flow of gas or liquid therethrough which are suitably connected to the ends of the tubing and then interconnected to one another so as to provide gas or liquid communication between the two sets of tubing. Oftentimes, one of the coupling parts is mounted on a panel.

There are several problems noted with current multiple tube connectors. For example, many multiple tube connectors have a threaded fastener to connect the two coupling parts. Threaded fasteners sometimes require a substantial amount of time to be threaded to connect multiple tube connectors. Furthermore, threaded fasteners that are threaded at an incorrect angle may become cross-threaded and damaged. Additionally, threaded fasteners may be connected incorrectly, such that the two coupling parts connect the wrong tubes to each other. Moreover, if an appropriate substantially gas-tight or liquid-tight seal is desired between the coupling parts, the threaded fasteners need to be properly tightened. Depending on the person tightening the fasteners and/or the tools available, the degree to which the coupling parts are tightened may vary substantially.

Some multiple tube connectors are made from plastics materials and are injection molded to form a one piece multiple tube connector. These types of multiple tube connectors may break during use leaving the device unusable until a new multiple tube connector is installed to replace the broken multiple tube connector.

SUMMARY

The present application discloses one or more of the features recited in the appended claims and/or the following features which, alone or in any combination, may comprise patentable subject matter.

In a first aspect of the present disclosure, a multi-port connector for a respiratory therapy device includes a connector base, a receiver disk coupled to the connector base, and a plurality of barbed conduits. The receiver disk being formed to include a plurality of apertures with a first diameter, each of the plurality of barbed conduits including a retainer section with a second diameter that is greater than the first diameter so that each barbed conduit forms a friction-interference fit between the receiver disk and each retainer section.

In some embodiments of the first aspect, the receiver disk is coupled to the connector base for pivotable movement relative to the connector base about an axis between an unlocked orientation and a locked orientation and an adaptor is configured to be coupled to the plurality of barbed conduits when the receiver disk is in the unlocked orientation.

In some embodiments of the first aspect, the connector base includes a body plate with a central opening sized to receive the receiver disk and first and second retainer tabs coupled to the body plate on opposite sides of the central opening, the first and second retainer tabs providing first and second slots between the body plate and first and second retainer tabs.

In some embodiments of the first aspect, the adaptor includes an adaptor body and first and second lock tabs coupled to opposite sides of the adaptor body and that extend radially outward from the adaptor body in opposite directions, the first and second lock tabs being sized to extend into the first and second slots when the adaptor is coupled to the plurality of barbed conduits and the receiver disk is subsequently rotated to the locked orientation.

In some embodiments of the first aspect, the receiver disk and the plurality of barbed conduits comprise metallic materials. In some embodiments of the first aspect, the receiver disk and the plurality of barbed conduits comprise stainless steel.

In some embodiments of the first aspect, the second diameter is sized selectively so that the friction-interference fit is able to withstand a predetermined pull force. In some embodiments of the first aspect, the predetermined pull force is at least 200 Newtons. In some embodiments of the first aspect, the second diameter is about 0.34% larger than the first diameter to provide the friction-interference fit.

In some embodiments of the first aspect, the receiver disk is formed to include a first detent notch and a second detent notch spaced apart circumferentially from the first detent notch by about 45 degrees about the axis. In some embodiments of the first aspect, the first detent notch and the second detent notch are formed in a back side of the receiver disk and extend inwardly from an outer edge of the receiver disk toward the axis.

In some embodiments of the first aspect, the connector base includes a detent tab that engages the first detent notch when the receiver disk is in the unlocked orientation and engages the second detent notch when the receiver disk is in the locked orientation.

In some embodiments of the first aspect, each of the plurality of barbed conduits includes a first spot weld and a second spot weld each located at interface points between the receiver disk and the retainer section along a back side of the receiver disk.

In some embodiments of the first aspect, the first spot weld and the second spot weld are located on opposite sides of each barbed conduit.

In some embodiments of the first aspect, each of the plurality of barbed conduits further includes a slot section directly adjacent to the retainer section, and each slot section is sized to receive a clip that engages a back side of the receiver disk and an edge of the slot section.

In some embodiments of the first aspect, the receiver disk is formed to include a guide slot with a first rectangular portion that extends along a first axis and second portion opening into the first portion that extends along a second axis that is perpendicular to the first axis. In some embodiments of the first aspect, the adaptor includes a guide post with a shape that matches the guide slot.

According to a second aspect of the present disclosure, a respiratory therapy device includes a respiratory control unit, a respiratory circuit, and a multi-port connector. The respiratory control unit is configured to provide at least one respiratory therapy for a user. The respiratory circuit is coupled to the respiratory control unit to deliver the respiratory therapy to the user and includes an adaptor configured to be coupled to the connector base. The multi-port connector interconnecting the respiratory circuit to the respiratory control unit.

In some embodiments of the second aspect, the multi-port connector includes a connector base coupled to the respiratory control unit, a receiver disk coupled to the connector base, and a plurality of barbed conduits coupled to the receiver disk. The receiver disk is formed to include a plurality of apertures with a first diameter. Each of the plurality of barbed conduits include a retainer section with a second diameter greater than the first diameter so that each barbed conduit forms a friction-interference fit between the receiver disk and the retainer section.

In some embodiments of the second aspect, the receiver disk is coupled to the connector base for pivotable movement relative to the connector base about an axis between an unlocked orientation and a locked orientation and the adaptor is configured to be coupled to the plurality of barbed conduits when the receiver disk is in the unlocked orientation.

In some embodiments of the second aspect, the connector base includes a body plate with a central opening sized to receive the receiver disk and first and second retainer tabs coupled to the body plate on opposite sides of the central opening, the first and second retainer tabs providing first and second slots between the body plate and first and second retainer tabs.

In some embodiments of the second aspect, the adaptor includes an adaptor body and first and second lock tabs coupled to opposite sides of the adaptor body and that extend radially outward from the adaptor body in opposite directions, the first and second lock tabs being sized to extend into the first and second slots when the adaptor is coupled to the plurality of barbed conduits and the receiver disk is subsequently rotated to the locked orientation.

In some embodiments of the second aspect, the receiver disk and the plurality of barbed conduits comprise metallic materials. In some embodiments of the second aspect, the receiver disk and the plurality of barbed conduits comprise stainless steel.

In some embodiments of the second aspect, the second diameter is sized selectively so that the friction-interference fit is able to withstand a predetermined pull force. In some embodiments of the second aspect, the predetermined pull force is at least 200 Newtons. In some embodiments of the second aspect, the second diameter is about 0.34% larger than the first diameter to provide the friction-interference fit.

In some embodiments of the second aspect, the receiver disk is formed to include a first detent notch and a second detent notch spaced apart circumferentially from the first detent notch by about 45 degrees about the axis. In some embodiments of the second aspect, the first detent notch and the second detent notch are formed in a back side of the receiver disk and extend inwardly from an outer edge of the receiver disk toward the axis. In some embodiments of the second aspect, the connector base includes a detent tab that engages the first detent notch when the receiver disk is in the unlocked orientation and engages the second detent notch when the receiver disk is in the locked orientation.

In some embodiments of the second aspect, each of the plurality of barbed conduits includes a first spot weld and a second spot weld each located at interface points between the receiver disk and the retainer section along a back side of the receiver disk. In some embodiments of the second aspect, the first spot weld and the second spot weld are located on opposite sides of each barbed conduit.

In some embodiments of the second aspect, each of the plurality of barbed conduits further includes a slot section directly adjacent to the retainer section, and each slot section is sized to receive a clip that engages a back side of the receiver disk and an edge of the slot section.

In some embodiments of the second aspect, the receiver disk is formed to include a guide slot with a first rectangular portion that extends along a first axis and second portion opening into the first portion that extends along a second axis that is perpendicular to the first axis. In some embodiments of the second aspect, the adaptor includes a guide post with a shape that matches the guide slot.

According to a third aspect of the present disclosure, a method of forming a quick disconnect multi-port connector for a respiratory therapy device includes providing a disk made from metallic materials. The method may further include machining a plurality of apertures through the disk. The method may further include providing a plurality of tubes made from metallic materials. The method may further include machining each of the tubes to include an outer surface with a plurality of barb sections and an inner surface defining a fluid passageway that extends through each of the tubes, one of the barb sections forming a retainer section with an outer diameter that is greater than each of the apertures formed in the disk. The method may further include inserting one of the plurality of tubes into each aperture formed in the disk, the retainer section of each of the plurality of tubes interfacing with a wall defining each aperture to form a friction-interference fit between the disk and the retainer section to couple each tube to the disk.

In some embodiments of the third aspect, the step of spot welding each of the tubes to the disk at an interface point between the retainer section and the disk.

In some embodiments of the third aspect, each tube has a first spot weld on a first side of the tube at the interface point between the retainer section and the disk and a second spot weld on a second side of the tube opposite the first side at the interface point between the retainer section and the disk.

In some embodiments of the third aspect, the step of machining each of the tubes further includes machining a slot section into each tube adjacent to each retainer section and the step of inserting further includes inserting a clip into the slot section between the disk and an edge of the slot section.

In some embodiments of the third aspect, the step of machining the apertures in the disk further includes polishing the walls defining each of the apertures to remove sharp edges.

In some embodiments of the third aspect, the metallic materials of the disk and the plurality of tubes comprise stainless steel.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

Figure 1:
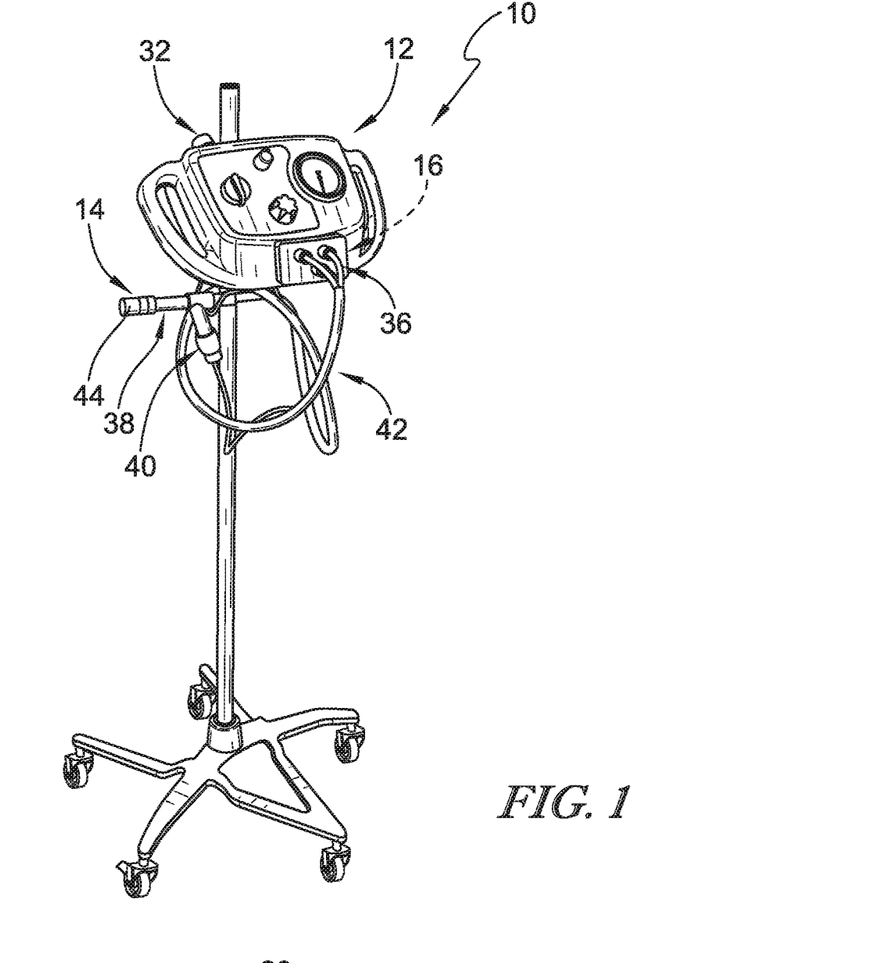
FIG. 1 is a perspective view of a respiratory therapy device in accordance with the present disclosure, including a respiratory control unit and a respiratory circuit coupled to the respiratory control unit.

Referring to FIG. 1, a respiratory therapy device 10 is shown and is used by a respiratory therapist to deliver one or more respiratory therapies to a patient. The respiratory therapy device 10 includes respiratory control unit 12, a respiratory circuit 14, and a multi-port connector 16. The respiratory control unit 12 is configured to provide the respiratory therapy. The respiratory therapy may include delivering a medicated aerosol or applying a composite therapy involving alternation between continuous high frequency oscillation (CHFO) therapy and continuous positive expiratory pressure (CPEP) therapy each in conjunction with the aerosol delivery. The respiratory circuit 14 is configured to deliver the respiratory therapy to the patient from the respiratory control unit 12. An example of a suitable respiratory control unit 12 and associated respiratory circuit 14 is shown and described in U.S. Pat. No. 9,675,775, issued on Jun. 13, 2017, which is expressly incorporated by reference herein in its entirety for the purpose of describing a suitable respiratory control unit 12 and respiratory circuit 14.

The respiratory control unit 12 includes a housing 18 that contains associated control unit equipment (not shown) for providing the respiratory therapy. The respiratory control unit 12 further includes a plurality of visible components on an outer surface 24 of the housing 18. The visible components include a pressure manometer 26, an intensity switch 28 for selecting between a higher and lower percussive intensity, a mode selector 30 for selecting between modes, an oxygen gas connector 32, and a flow adjustor 34 for regulating an amount of oxygen flow when in the CPEP mode. The oxygen gas connector 32 is configured to be coupled to an external gas source such as a canister or a port on a wall in a healthcare facility.

The respiratory circuit 14 includes an adaptor 36 that is configured to be coupled removably with the multi-port connector 16 as show in FIG. 1. The respiratory circuit 14 further includes a handset 38, a nebulizer unit 40, and a plurality of tubular conduits 42 interconnecting the adaptor 36 to the handset 38 and nebulizer unit 40. The handset 38 includes a mouthpiece 44 that the patient uses to receive the respiratory therapy when the respiratory circuit 14 is coupled to the respiratory control unit 12 and the respiratory control unit 12 is on. The nebulizer unit 40 is configured to convert a liquid medication into a mist so that the patient may breathe the medication into their lungs for the treatment of various conditions. However, in some embodiments, the respiratory circuit 14 may not include the nebulizer unit 40. The plurality of conduits 42 are configured to transfer fluid, i.e. oxygen, from the respiratory control unit 12 to the handset 38 and/or the nebulizer unit 40. In the illustrative embodiment, one of the conduits 42 is used for pressure sensing while the remaining two conduits 42 conduct the fluid therethrough for treatment purposes.

Figure 2:
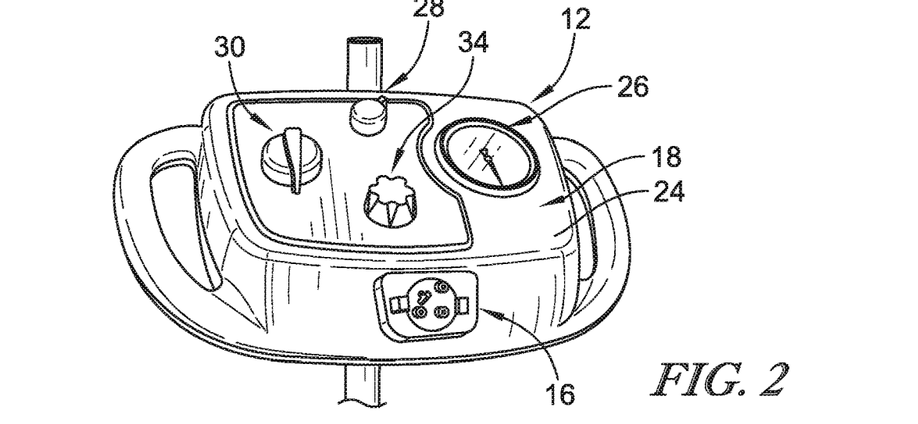
FIG. 2 is an enlarged view of the respiratory control unit from FIG. 1 with the respiratory circuit de-coupled from the respiratory control unit to show a portion of a multi-port connector coupled to the respiratory control unit.
Figure 3:
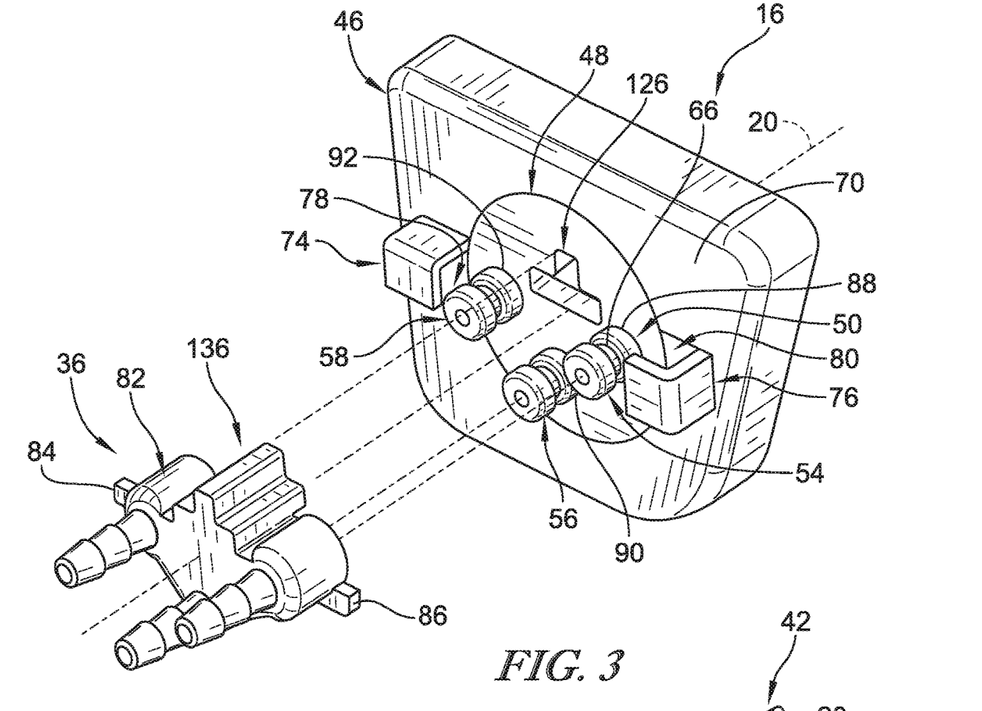
FIG. 3 is an exploded assembly view of the multi-port connector including an adaptor coupled to the respiratory circuit and a connector base coupled to the respiratory control unit.
Figure 4:
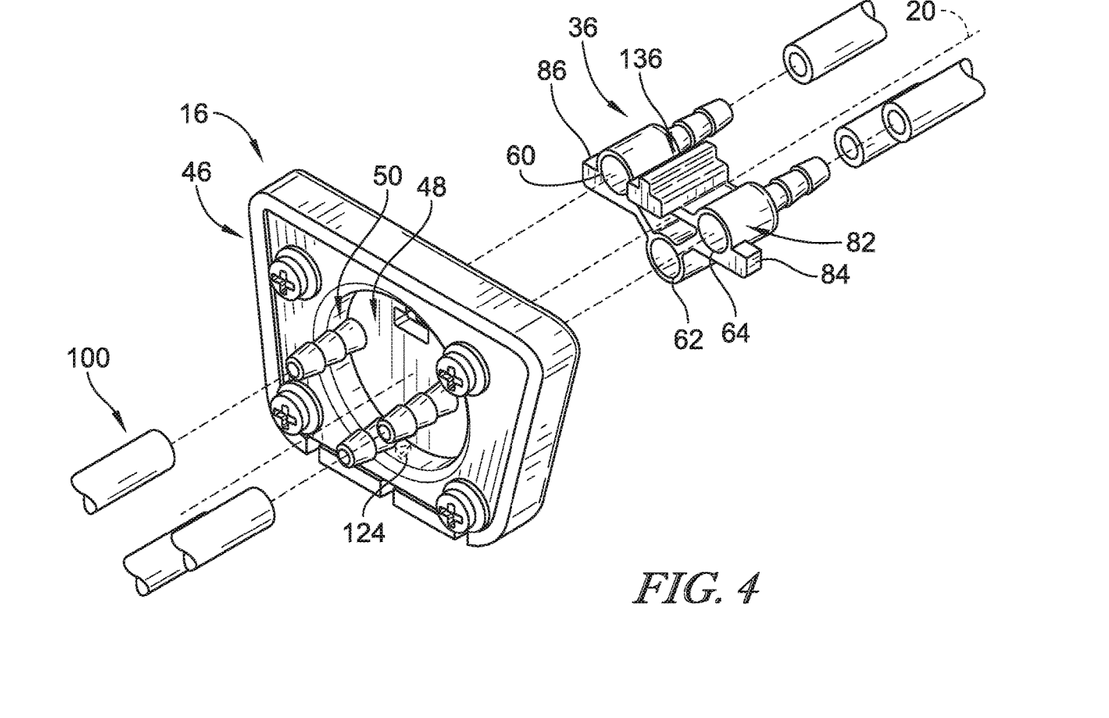
FIG. 4 is another exploded assembly view of the multi-port connector in a different orientation.
Figure 5:
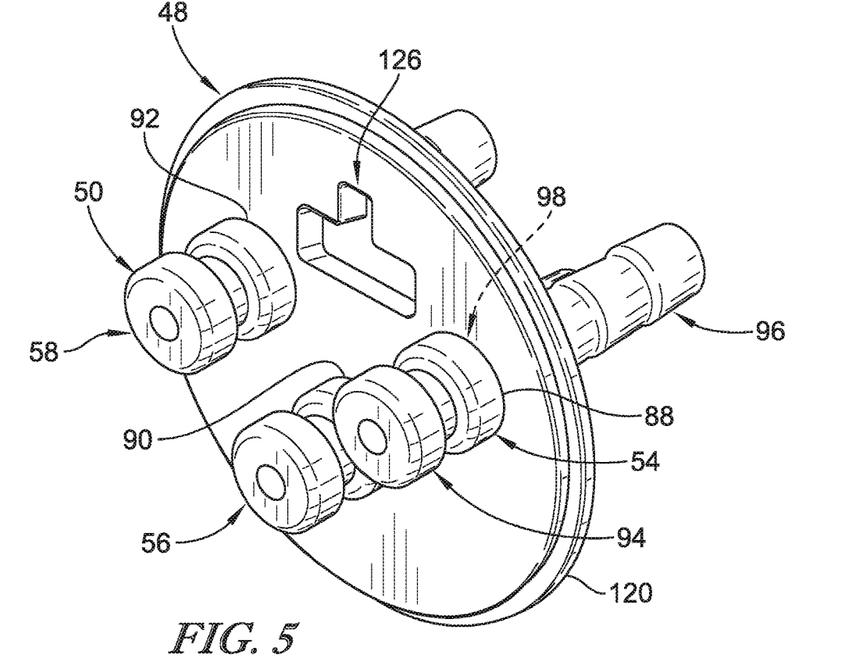
FIG. 5 is an enlarged perspective view of a receiver disk included in the connector base of FIGS. 3 and 4.

The multi-port connector 16 is also mounted to the outer surface 24 of the housing 18 and is configured to receive the adaptor 36 of the respiratory circuit 14 to couple the respiratory circuit 14 to the respiratory control unit 12. The multi-port connector includes a connector base 46, a receiver disk 48, and a plurality of barbed conduits 50 as shown in FIGS. 2-4. The connector base 46 is mounted to the respiratory control unit 12 in a generally central, accessible area. The receiver disk 48 coupled to the connector base 46 for pivotable movement relative to the connector base 46 about an axis 20 between an unlocked orientation and a locked orientation. The plurality of barbed conduits 50 are coupled to the receiver disk 48 for movement with the receiver disk 48 relative to the connector base 46 between the unlocked orientation and the locked orientation.

The multi-port connector 16 and the adaptor 36 cooperate to provide a quick connect system for the coupling the respiratory circuit 14 to the respiratory control unit 12. The plurality of barbed conduits 50 illustratively include three barbed conduits 54, 56, 58 mounted on the receiver disk 48 in a generally triangular arrangement. The adaptor 36 is formed to include three corresponding openings 60, 62, 64 that are each sized and arranged to receive one of the barbed conduits 54, 56, 58 when the receiver disk 48 is in arranged in the unlocked orientation. With the openings 60, 62, 64 aligned with the barbed conduits 54, 56, 58, the adaptor 36 may be pressed onto the multi-port connector such that a portion of each barbed conduit 54, 56, 58 extends into each corresponding opening 60, 62, 64. Each of the barbed conduits 54, 56, 58 is configured to receive a seal ring (not shown) in a slot 66 to provide an annular sealing interface between an inner surface defining each opening 60, 62, 64 and the barbed conduits 54, 56, 58. Once connected to the plurality of barbed conduits 50, the adaptor 36 and receiver disk 48 may be rotated from the unlocked orientation to the locked orientation to block removal of the adaptor 36 from the multi-port connector 16.

The connector base 46 cooperates with the adaptor 36 to block removal of the adaptor 36 from the multi-port connector 16 in the locked orientation. The connector base 46 includes a body plate 70 that is formed to include a central aperture 72, a first retainer tab 74, and a second retainer tab 76. The body plate 70 is mounted to the housing 18 of the respiratory control unit 12 and is configured to retain the receiver disk 48 in the central aperture 72. The first retainer tab 74 is coupled to an external surface of the body plate 70 on a first side of the central aperture 72. The second retainer tab 76 is coupled to the external surface of the body plate 70 on a second side of the central aperture 72 opposite the first side. Each retainer tab 74, 76 defines a slot 78, 80 between the body plate 70 and the retainer tab 74, 76. The slots 78, 80 open radially inwardly toward the axis 20. The slot 78 defined by the first retainer tab 74 opens downwardly while the slot 80 defined by the second retainer tab 76 opens upwardly.

The adaptor 36 includes an adaptor body 82 and first and second lock tabs 84, 86 that extend outwardly from the adaptor body 82. The first and second lock tabs 84, 86 are sized to correspond with the slots 78, 80 defined by the first and second retainer tabs 74, 76. The retainer tabs 74, 76 block the adaptor 36 from being coupled with the plurality of barbed conduits 50 when the receiver disk 48 is arranged in the locked orientation. In the unlocked orientation, the lock tabs 84, 86 are offset from the retainer tabs 74, 76 and the adaptor 36 may be coupled with the plurality of barbed conduits 50. Once coupled with the plurality of barbed conduits 50, the adaptor 36 and the receiver disk 48 may be rotated in a clockwise direction to the locked orientation so that the lock tabs 84, 86 are moved into each corresponding slot 78, 80. In the locked orientation, the retainer tabs 74, 76 block movement of the lock tabs 84, 86 along the axis 20 to block removal of the adaptor 36 from the plurality of barbed conduits 50.

In the illustrative embodiment, the receiver disk 48 and each of the barbed conduits 54, 56, 58 are formed as separate components from one another. The receiver disk 48 and each of the barbed conduits 54, 56, 58 are assembled subsequently to facilitate manufacture of the receiver disk 48 and each of the barbed conduits 54, 56, 58. The receiver disk 48 and each of the barbed conduits 54, 56, 58 are made from metallic materials such as stainless steel, for example. In some embodiments, the materials forming the receiver disk 48 and each of the barbed conduits 54, 56, 58 consist of stainless steel. The metallic materials provide a robust receiver disk 48 and conduits 50 which would be subject to wear and tear if made from plastics materials and formed as one piece.

The receiver disk 48 is illustratively formed as a metallic plate and is machined so that it is formed to include a plurality of conduit apertures 88, 90, 92 as shown in FIGS. 3 and 4. Each aperture 88, 90, 92 is sized to receive a corresponding barbed conduit 54, 56, 58 and couple each of the barbed conduits 54, 56, 58 to the receiver disk 48 with a friction-interference fit. In the illustrative embodiment, the friction-interference fit between the receiver disk 48 and each of the barbed conduits 54, 56, 58 is designed to withstand a predetermined pull force. The predetermined pull force is designed to prevent the barbed conduits 54, 56, 58 from being removed from the receiver disk while decoupling the adaptor 36 from the barbed conduits 54, 56, 58. In some embodiments, the predetermined pull force is at least 200 Newtons.

Each of the barbed conduits in the illustrative embodiment are identical. Accordingly, only one barbed conduit 54 is described below and the features described for barbed conduit 54 are hereby incorporated by reference for barbed conduits 56 and 58. The barbed conduit 54 includes a generally cylindrical head section 94, a barbed section 96, and a retainer section 98 as shown in FIGS. 5-8. The head section 94 protrudes axially away from from the receiver disk 48 relative to the axis 20 so that it is accessible at an exterior of the housing 18 for receiving the adaptor 36. The barbed section 96 extends axially away from the receiver disk 48 into the housing 18. The barbed section 96 is configured receive a corresponding conduit 100 for conducting fluid through the multi-port connector 16 from the respiratory control unit 12 to the respiratory circuit 14. The retainer section 98 interconnects the head section 94 and the barbed section 96 and engages the receiver disk 48 to provide the friction-interference fit between the barbed conduit 54 and the receiver disk 48.

Figure 8:
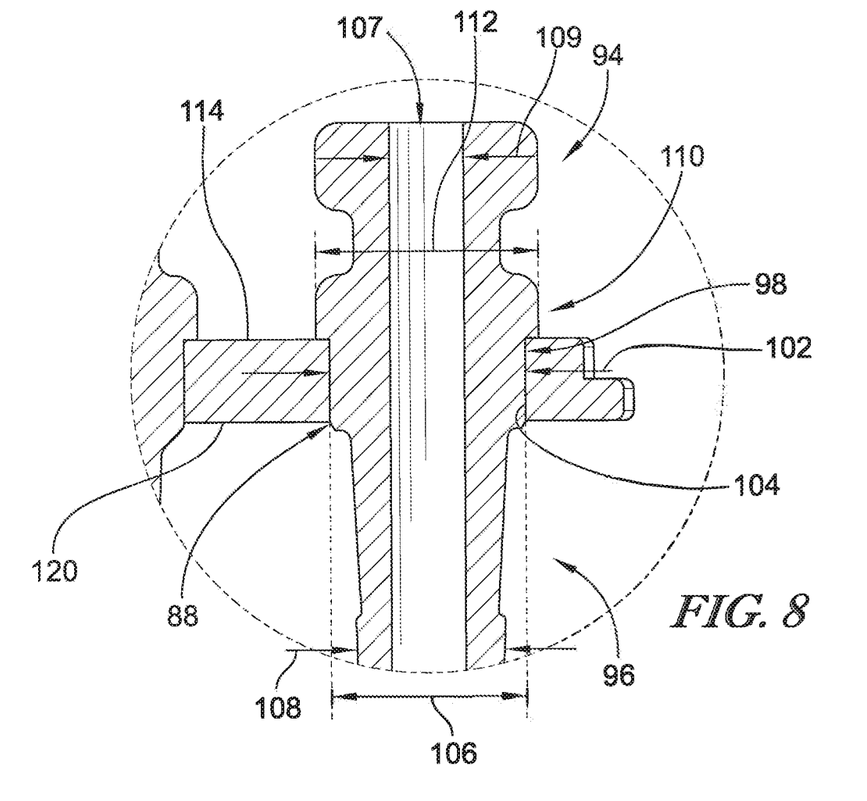
FIG. 8 is an enlarged sectional view of the circled region in FIG. 7 showing one of the plurality of barbed conduits coupled to the disk body with a friction-interference fit.

The retainer section 98 has an outer diameter 102 while the corresponding aperture 88 that receives the barbed conduit 54 is defined by a wall 104 with an inner diameter 106 as shown in FIG. 8. The outer diameter 102 of the retainer section 98 is greater than the inner diameter 106 of the wall 104 defining the aperture 88. The outer diameter 102 of the retainer section and the inner diameter 106 of the wall 104 defining the aperture 88 are sized selectively to provide the friction-interference fit that withstands the predetermined pull force.

In the illustrative embodiment, the outer diameter 102 is greater than or equal to about 5.8 mm. In some embodiments, the outer diameter 102 is within a range of 5.819 mm to 5.827 mm. In the illustrative embodiment, the inner diameter 106 is equal to about 5.8 mm. In some embodiments, the outer diameter 102 is within a range of 5.8 mm to 5.812 mm. In some embodiments, the outer diameter 102 is about 0.34% larger than the inner diameter 106 to provide the friction-interference fit with the predetermine pull force. The percent difference between the outer diameter 102 and the inner diameter 106 may vary due to the tolerances described above.

An outermost diameter 108 of the barbed section 96 is less than the inner diameter 106 so that the barbed conduit 54 may be inserted through the aperture 88 with the barbed section 96 extending therethrough first. The head section 94 includes a shoulder 110 positioned directly adjacent to the retainer section 98. The shoulder 110 has an outer diameter 112 that is greater than the outer diameter 102 of the retainer section 98. The retainer section 98 of the barbed conduit 54 is press fit through the aperture 88 to provide the friction-interference fit until an outer surface 114 of the receiver disk 48 engages the shoulder 110 of the head section 94. In some embodiments, the shoulder 110 may be omitted and the retainer section 98 may gradually increase in diameter such that, when press fit through the aperture 88, the increase in diameter stops further insertion of the barbed conduit 54 at a predetermined point.

A fluid passageway 107 extends through the barbed conduit 54 and has a substantially constant diameter 109 as shown in FIG. 8. The diameter 109 in the illustrative embodiment is equal to about 2.25 mm with a bi-directional tolerance of about 0.05 mm. The diameter 109 is sized to conduct fluid therethrough in a manner that provides the adequate respiratory therapy performance from the respiratory control unit 12. In other embodiments, the diameter 109 may vary to provide desired fluid properties for other settings in which the multi-port connector 16 is used.

Figure 6:
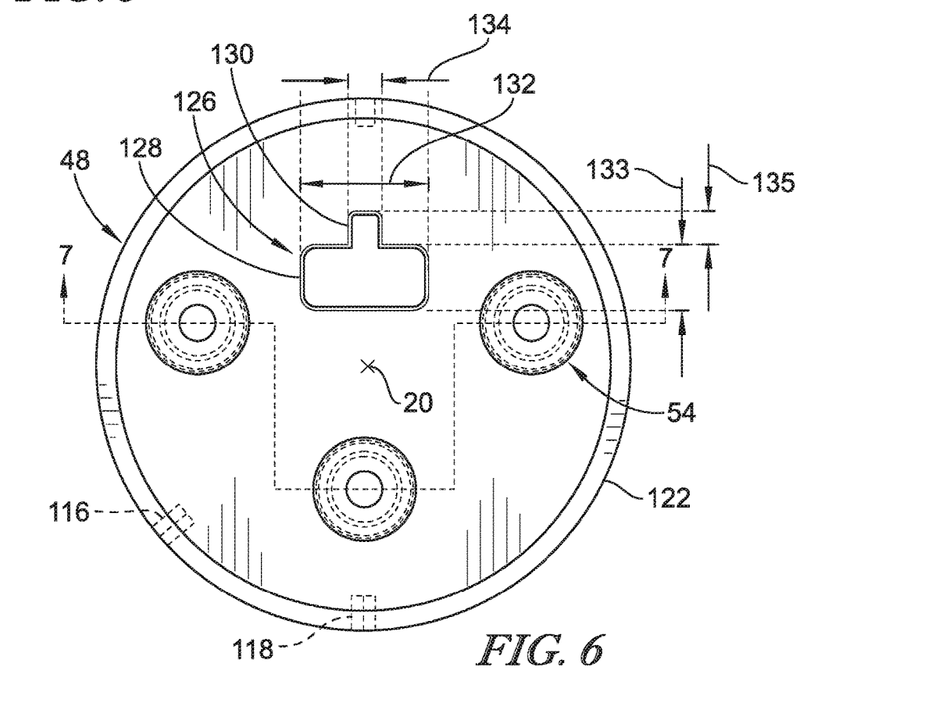
FIG. 6 is an elevation view of the receiver disk showing that the receiver disks is formed to include a guide slot.
Figure 7:
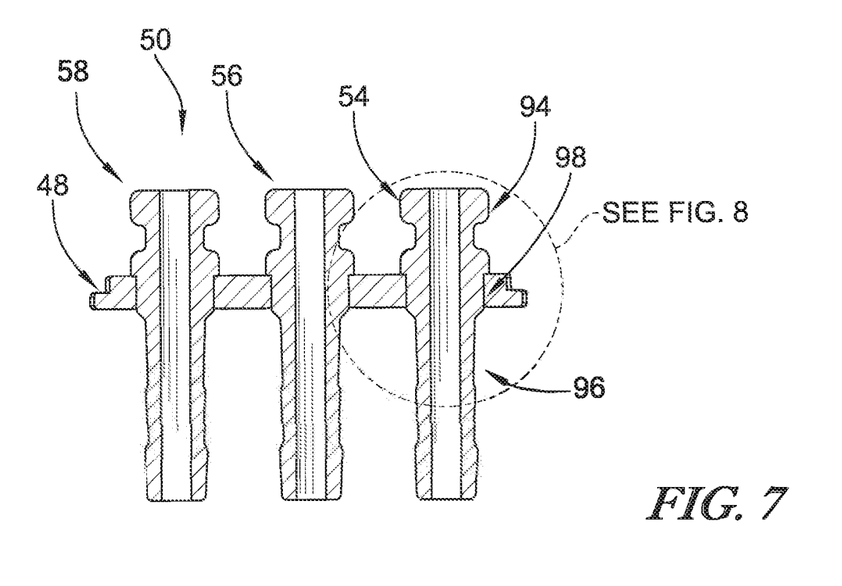
FIG. 7 is a sectional view taken along line 7-7 in FIG. 6 showing that the receiver disk includes a disk body and a plurality of barbed conduits.

The receiver disk 48 is also formed to include a first detent notch 116 and a second detent notch 118 spaced apart circumferentially from the first detent notch 116 about the axis 20 as shown in FIG. 6. The first detent notch 116 and the second detent notch 118 are formed in a back side 120 of the receiver disk and extend inwardly from an outer edge 122 of the receiver disk 48 toward the axis 20. In the illustrative embodiment, the first and second detent notches 116, 118 are spaced apart from one another by about 45 degrees. The connector base 46 includes a fixed detent tab 124 that engages the first detent notch 116 when the receiver disk 48 is in the unlocked orientation and engaged the second detent notch 118 when the receiver disk 48 is in the locked orientation as shown in FIG. 4.

In the illustrative embodiment, the receiver disk 48 is also formed to include a guide slot 126 as shown in FIGS. 3-6. The guide slot 126 is defined by a first rectangular portion 128 and second arm portion 130. The rectangular portion 128 extends transversely along the receiver disk 48 and has a length 132 and a height 133. The arm portion 130 opens into the rectangular portion 128 and extends away from the rectangular portion 128 generally perpendicular to the rectangular portion 128. The arm portion 130 is located about midway along the length 132 of the rectangular portion 128 and has a length 134 and a height 135. The length 132 of the rectangular portion 128 is greater than the length 134 of the arm portion 130. The height 133 of the rectangular portion 128 is greater than the height 135 of the arm portion 130.

The adaptor 36 further includes a guide post 136 with a shape that matches the guide slot 126 as shown in FIG. 4. The guide post 136 facilitates coupling of the adaptor 36 with the plurality of barbed conduits 50 in the proper orientation. The guide post 136 also supports loads acting on the adaptor 36 as the adaptor 36 and the receiver disk 48 are moved between the unlocked orientation and the locked orientation.

Figure 9:
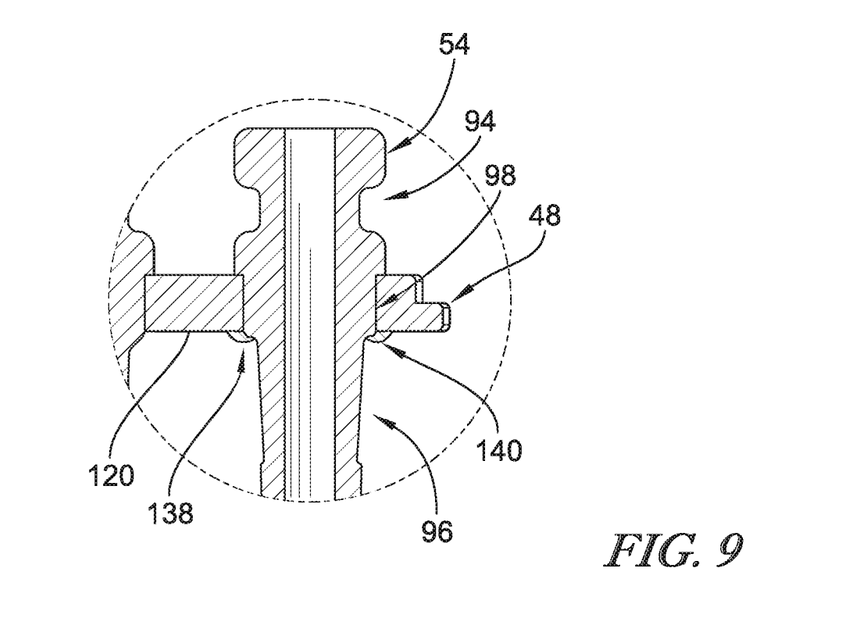
FIG. 9 is an enlarged sectional view similar to FIG. 8 showing one of the plurality of barbed conduits coupled to the disk body with a friction-interference fit and with a pair of spot welds.
Figure 10:
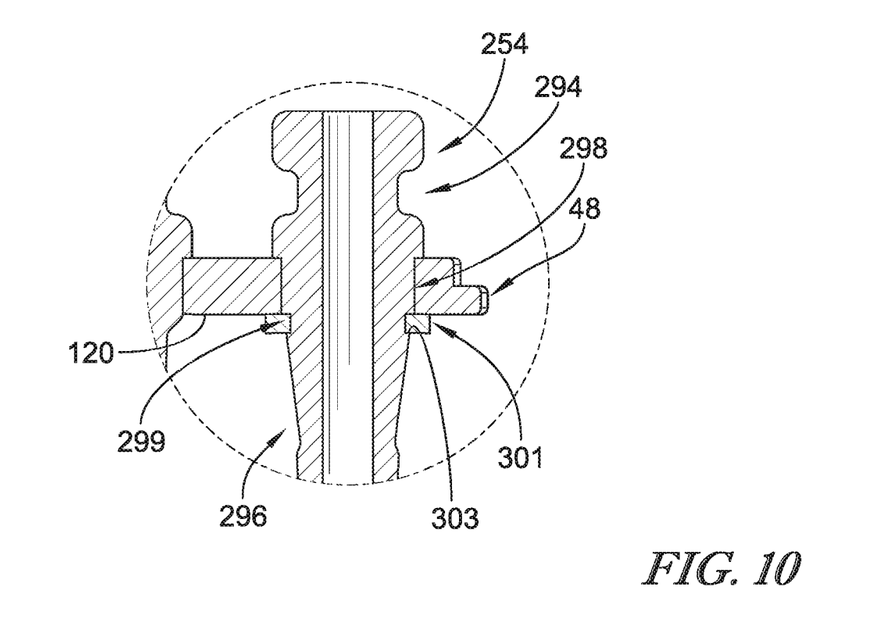
FIG. 10 is an enlarged sectional view similar to FIGS. 7 and 8 showing another embodiment of a barbed conduit coupled to the disk body using a clip.

In some embodiments, the friction-interference fit between each of the barbed conduits 54, 56, 58 and the receiver disk 48 may be reinforced as shown in FIGS. 9 and 10. For example, the barbed conduit 54 may include at least one spot weld 138, 140 between the receiver disk 48 and the barbed conduit 54. In the illustrative embodiment shown in FIG. 9, a first spot weld 138 and a second spot weld 140 are located at interface points between the receiver disk 48 and the retainer section along the back side 120 of the receiver disk 48. The first spot weld 138 and the second spot weld 140 are located on opposite sides of the barbed conduit 54 from one another. It should be appreciated that any suitable number of spot welds may be used. Other types of metal joining processes may also be used such as brazing and soldering, for example.

In the illustrative embodiment, the multi-port connector 16 is used with a respiratory therapy device 10. However, it should be appreciated that the illustrative multi-port connector 16 described herein may be used in other settings that require a multi-port connection.

Another embodiment of a barbed conduit 254 is shown in FIG. 10. The barbed conduit 254 is similar to barbed conduit 54 shown in FIGS. 3-9 and described above. The barbed conduit 254 includes a head section 294, a barbed section 296, a retainer section 298, and a slot section 299. The slot section 299 is positioned directly adjacent to the retainer section 298 and the back side 120 of the receiver disk 48. The slot section 299 is sized to receive a clip 301 that engages the back side 120 of the receiver disk 48 and an edge 303 of the slot section 299. The clip 301 is illustratively embodied as a circlip and helps retain the barbed conduit 254 to the receiver disk 48 in conjunction with the friction-interference fit between the retainer section 298 and the receiver disk 48.

Although certain illustrative embodiments have been described in detail above, variations and modifications exist within the scope and spirit of this disclosure as described and as defined in the following clauses and claims.

The invention claimed is:

1. A respiratory therapy device comprising
   a respiratory control unit configured to provide at least one respiratory therapy for a user,
   a respiratory circuit coupled to the respiratory control unit to deliver the respiratory therapy to the user, the respiratory circuit including an adaptor, and
   a multi-port connector interconnecting the respiratory circuit to the respiratory control unit, the multi-port connector comprising,
      a connector base coupled to the respiratory control unit,
      a receiver disk coupled to the connector base, and
      a plurality of barbed conduits coupled to the receiver disk and adapted to be coupled to the adaptor, each of the barbed conduits including a head section adapted to couple with the adaptor, a barbed section opposite the head section, and a retainer section interconnecting the head section and the barbed section and engaged with the receiver disk,
   wherein the receiver disk is formed to include a plurality of apertures with a first diameter, and the retainer section of each of the plurality of barbed conduits has a second diameter greater than the first diameter so that each barbed conduit forms a friction-interference fit between the receiver disk and the retainer section,
   wherein the barbed section has an outermost diameter less than the first diameter and the second diameter to allow insertion of each of the plurality of barbed conduits through a respective aperture included in the plurality of apertures, and the head section includes a shoulder having a third diameter greater than the first diameter and the second diameter so that the shoulder engages an outer surface of the receiver disk when each of the plurality of barbed conduits are inserted through each respective aperture in a first direction, and
   wherein the second diameter is sized selectively so that the friction-interference fit is able to withstand a predetermined pull force of at least 200 Newtons to block removal of the plurality of barbed conduits out of each respective aperture in a second direction opposite the first direction absent the predetermined pull force.

2. The respiratory therapy device of claim 1, wherein the receiver disk is coupled to the connector base for pivotable movement relative to the connector base about an axis between an unlocked orientation and a locked orientation and the adaptor is configured to be coupled to the plurality of barbed conduits when the receiver disk is in the unlocked orientation.

3. The respiratory therapy device of claim 2, wherein the connector base includes a body plate with a central opening sized to receive the receiver disk and first and second retainer tabs coupled to the body plate on opposite sides of the central opening, the first and second retainer tabs providing first and second slots between the body plate and first and second retainer tabs.

4. The respiratory therapy device of claim 3, wherein the adaptor includes an adaptor body and first and second lock tabs coupled to opposite sides of the adaptor body and that extend radially outward from the adaptor body in opposite directions, the first and second lock tabs being sized to extend into the first and second slots when the adaptor is coupled to the plurality of barbed conduits and the receiver disk is subsequently rotated to the locked orientation.

5. The respiratory therapy device of claim 1, wherein the receiver disk and the plurality of barbed conduits comprise metallic materials.

6. The respiratory therapy device of claim 5, wherein the receiver disk and the plurality of barbed conduits comprise stainless steel.

7. The respiratory therapy device of claim 1, wherein the second diameter is about 0.34% larger than the first diameter to provide the friction-interference fit.

8. The respiratory therapy device of claim 2, wherein the receiver disk is formed to include a first detent notch and a second detent notch spaced apart circumferentially from the first detent notch by about 45 degrees about the axis.

9. The respiratory therapy device of claim 8, wherein the first detent notch and the second detent notch are formed in a back side of the receiver disk and extend inwardly from an outer edge of the receiver disk toward the axis.

10. The respiratory therapy device of claim 8, wherein the connector base includes a detent tab that engages the first detent notch when the receiver disk is in the unlocked orientation and engages the second detent notch when the receiver disk is in the locked orientation.

11. The respiratory therapy device of claim 1, wherein each of the plurality of barbed conduits includes a first spot weld and a second spot weld each located at interface points between the receiver disk and the retainer section along a back side of the receiver disk.

12. The respiratory therapy device of claim 11, wherein the first spot weld and the second spot weld are located on opposite sides of each barbed conduit.

13. The respiratory therapy device of claim 1, wherein the receiver disk is formed to include a guide slot with a first rectangular portion that extends along a first axis and a second portion opening into the first portion that extends along a second axis that is perpendicular to the first axis.

14. A respiratory therapy device comprising
a respiratory control unit configured to provide at least one respiratory therapy for a user,
a respiratory circuit coupled to the respiratory control unit to deliver the respiratory therapy to the user, the respiratory circuit including an adaptor, and
a multi-port connector interconnecting the respiratory circuit to the respiratory control unit, the multi-port connector comprising,
a connector base coupled to the respiratory control unit,
a receiver disk coupled to the connector base, and
a plurality of barbed conduits coupled to the receiver disk and adapted to be coupled to the adaptor, each of the barbed conduits including a head section adapted to couple with the adaptor, a barbed section opposite the head section, and a retainer section interconnecting the head section and the barbed section and engaged with the receiver disk
wherein the receiver disk is formed to include a plurality of apertures with a first diameter, and the retainer section of each of the plurality of barbed conduits has a second diameter greater than the first diameter so that each barbed conduit forms a friction-interference fit between the receiver disk and the retainer section,
wherein the barbed section has an outermost diameter less than the first diameter and the second diameter to allow insertion of each of the plurality of barbed conduits through a respective aperture included in the plurality of apertures, and the head section includes a shoulder having a third diameter greater than the first diameter and the second diameter so that the shoulder engages an outer surface of the receiver disk when each of the plurality of barbed conduits are inserted through each respective aperture in a first direction, and
wherein the receiver disk is formed to include a guide slot with a first rectangular portion that extends along a first axis and a second portion opening into the first portion that extends along a second axis that is perpendicular to the first axis, and
wherein the adaptor includes a guide post with a shape that matches the guide slot and that is inserted into the first rectangular portion and the second portion of the guide slot when the adaptor is coupled with the multi-port connector.

15. The respiratory therapy device of claim 1, wherein each of the plurality of barbed conduits has a fluid passageway extending therethrough with a substantially constant diameter that is equal to about 2.25 mm.

16. The respiratory therapy device of claim 1, wherein the receiver disk is coupled to the connector base for pivotable movement relative to the connector base about an axis between an unlocked orientation and a locked orientation and the adaptor is configured to be coupled to the plurality of barbed conduits when the receiver disk is in the unlocked orientation, wherein the receiver disk is formed to include a first detent notch and a second detent notch spaced apart circumferentially from the first detent notch by about 45 degrees about the axis.

17. A respiratory therapy device comprising
a respiratory control unit configured to provide at least one respiratory therapy for a user,
a respiratory circuit coupled to the respiratory control unit to deliver the respiratory therapy to the user, the respiratory circuit including an adaptor, and
a multi-port connector interconnecting the respiratory circuit to the respiratory control unit, the multi-port connector comprising,
a connector base coupled to the respiratory control unit,
a receiver disk coupled to the connector base and is formed to include a first detent notch and a second detent notch spaced apart circumferentially from the first detent notch, and
a plurality of barbed conduits coupled to the receiver disk and adapted to be coupled to the adaptor, each of the barbed conduits including a head section adapted to couple with the adaptor, a barbed section opposite the head section, and a retainer section interconnecting the head section and the barbed section and engaged with the receiver disk
wherein the receiver disk is formed to include a plurality of apertures with a first diameter, and the retainer section of each of the plurality of barbed conduits has a second diameter greater than the first diameter so that each barbed conduit forms a friction-interference fit between the receiver disk and the retainer section,
wherein the barbed section has an outermost diameter less than the first diameter and the second diameter to allow insertion of each of the plurality of barbed conduits through a respective aperture included in the plurality of apertures, and the head section includes a shoulder having a third diameter greater than the first diameter and the second diameter so that the shoulder engages an outer surface of the receiver disk when each of the plurality of barbed conduits are inserted through each respective aperture in a first direction, and wherein the receiver disk is coupled to the connector base for pivotable movement relative to the connector base about an axis between an unlocked orientation and a locked orientation and the adaptor is configured to be coupled to the plurality of barbed conduits when the receiver disk is in the unlocked orientation, and wherein the first detent notch and the second detent notch are formed in a back side of the receiver disk and extend inwardly from an outer edge of the receiver disk toward the axis, and wherein the connector base includes a detent tab that engages the first detent notch when the receiver disk is in the unlocked orientation and engages the second detent notch when the receiver disk is in the locked orientation.

* * * * *